United States Patent
Hoshi et al.

(10) Patent No.: US 7,196,235 B2
(45) Date of Patent: Mar. 27, 2007

(54) PROCESS FOR PRODUCING FLUORINATED VINYL ETHER

(75) Inventors: Nobuto Hoshi, Fuji (JP); Nobuyuki Uematsu, Fuji (JP); Masanori Ikeda, Fuji (JP)

(73) Assignee: Asahi Kasei Kabushiki Kaisha, Osaka (JP)

( * ) Notice: Subject to any disclaimer, the term of this patent is extended or adjusted under 35 U.S.C. 154(b) by 232 days.

(21) Appl. No.: 10/482,048

(22) PCT Filed: Jun. 28, 2002

(86) PCT No.: PCT/JP02/06576

§ 371 (c)(1),
(2), (4) Date: Dec. 29, 2003

(87) PCT Pub. No.: WO03/002506

PCT Pub. Date: Jan. 9, 2003

(65) Prior Publication Data

US 2004/0176636 A1 Sep. 9, 2004

(30) Foreign Application Priority Data

Jun. 29, 2001 (JP) .................... 2001-198037
Jun. 29, 2001 (JP) .................... 2001-198038

(51) Int. Cl.
*C07C 21/18* (2006.01)

(52) U.S. Cl. .................. 570/136; 570/153; 570/216; 562/605

(58) Field of Classification Search ............ 570/134, 570/135, 136, 154, 200; 560/211, 213, 219, 560/226, 227
See application file for complete search history.

(56) References Cited

U.S. PATENT DOCUMENTS 3,282,875 A * 11/1966 Connolly et al. ........... 524/795
4,131,740 A * 12/1978 England .................... 560/180
4,153,804 A    5/1979 Yamabe et al.
4,329,435 A    5/1982 Kimoto et al.

FOREIGN PATENT DOCUMENTS

| DE | 2708677 A1 | 8/1978 |
|---|---|---|
| JP | 41-7949 B1 | 4/1966 |
| JP | 47-365 A | 1/1972 |
| JP | 52-78827 A | 7/1977 |
| JP | 52078827 * | 7/1977 |
| JP | 53-132519 | 11/1978 |
| JP | 54-112822 A | 9/1979 |
| JP | 55-31004 A | 3/1980 |
| JP | 56-90054 A | 7/1981 |
| JP | 60-156632 A | 8/1985 |
| JP | 7-505164 A | 6/1995 |

* cited by examiner

*Primary Examiner*—Johann Richter
*Assistant Examiner*—Karl Puttlitz
(74) *Attorney, Agent, or Firm*—Birch, Stewart, Kolasch & Birch, LLP

(57) ABSTRACT

There is provided a process for producing a fluorinated vinyl ether from a fluorinated acid fluoride compound having an ester group as a precursor of a carboxylic acid group, or a $SO_2F$ group as a precursor of a sulfonic acid group, in high yield by simple operations.

Said process is a production process comprising pyrolyzing a carboxylic acid potassium salt with a specific structure represented by the following formula in the absence of a solvent and/or while maintaining the salt in the solid state:

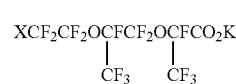

(1)

wherein X is —$CO_2R$ or —$SO_2F$, and R is an alkyl group.

13 Claims, No Drawings

PROCESS FOR PRODUCING FLUORINATED VINYL ETHER

TECHNICAL FIELD

The present invention relates to a process for producing a fluorinated vinyl ether, a starting monomer for a fluorine-containing ion-exchange membrane useful as a diaphragm for sodium chloride electrolysis or a diaphragm for a fuel cell.

BACKGROUND ART

The ion-exchange membrane process is widely employed in sodium chloride electrolysis for producing sodium hydroxide and chlorine. As an ion-exchange membrane which is a diaphragm for the electrolysis, a laminate type membrane of a perfluorocarbon sulfonic acid polymer and a perfluorocarbon carboxylic acid polymer is mainly used. In recent years, fuel cells using a solid polymer diaphragm as an electrolyte have been drawing attention because they can be miniaturized and lightened and can have a high power density at a relatively low temperature. The development of such fuel cells is accelerated for, in particular, the applications in automobiles. Also in the case of the fuel cells, a perfluorocarbon sulfonic acid polymer is employed as a solid electrolyte membrane at present in an attempt to put the fuel cells to practical use.

As a perfluorocarbon sulfonic acid polymer and a perfluorocarbon carboxylic acid polymer which are used in an ion-exchange membrane for sodium chloride electrolysis and a solid electrolyte membrane for a fuel cell, those having a structure represented by the following general formula (I) are common:

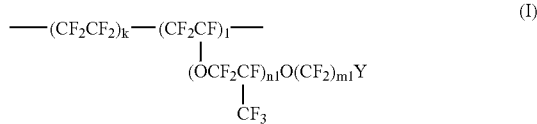

wherein $n^1=0$ to 1, $m^1=$an integer of 1 to 5, and $Y=$—$CO_2H$ or —$SO_3H$ (Haruhisa Miyake "Development of Fluoro Functional Materials", p. 105, CMC Co., Ltd., 1994). These polymers are obtained by forming a film of a copolymer of a fluorinated vinyl ether monomer represented by the following general formula (II):

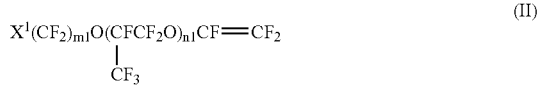

wherein $n^1$ and $m^1$ are as defined in the general formula (I), $X^1=$—$CO_2R^1$ or —$SO_2F$, and $R^1=$an alkyl group, and tetrafluoroethylene (TFE), and then hydrolyzing the film.

A typical process for producing the fluorinated vinyl ether monomer represented by the general formula (II) includes a process wherein a carboxylic acid fluoride represented by the general formula (III) is converted to a carboxylate represented by the general formula (IV) and then the carboxylate is pyrolyzed to form a perfluorovinyl group (a $CF_2=CF$— group) as follows:

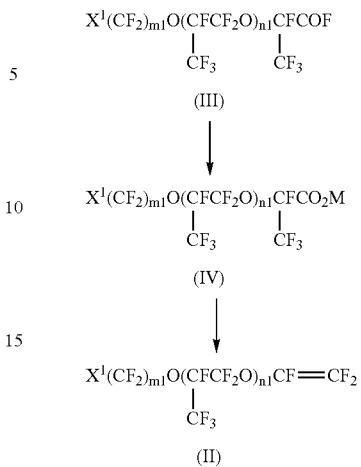

($n^1$, $m^1$ and $X^1$ in the general formula (III), (IV) are as defined in the general formula (II), and M in the general formula (IV) is a metal atom such as an alkali metal atom).

As such processes, there are known a process comprising feeding a carboxylic acid fluoride of the general formula (III) into heated alkali powder of sodium carbonate or the like to form the fluorinated vinyl ether monomer represented by the general formula (II) in one step via a carboxylate of the general formula (IV) (hereinafter referred to as the flow process), and a process comprising reacting a carboxylic acid fluoride of the general formula (III) with an alkali to convert the same to a carboxylate of the general formula (IV) once, and then heating the carboxylate to pyrolyze the same, to obtain the fluorinated vinyl ether monomer represented by the general formula (II) (hereinafter referred to as the two-stage process).

Firstly, conventional techniques for producing a fluorinated vinyl ether monomer represented by the general formula (II) wherein $X^1=CO_2R^1$ will be described.

As an example of the flow process in the case where $X^1=CO_2R^1$, JP-A-53-132519 discloses an example of the case where $n^1=1$ or 2, $m^1=2$, M=Na, and $X^1=CO_2CH_3$. According to this example, the vinyl ether monomer is obtained in a yield of 67% in the case where $n^1=1$, or in a yield of 61% in the case where $n^1=2$.

On the other hand, JP-A-52-78827 discloses an example of the two-stage process in the case where $X^1=CO_2R^1$, and reports the following results: the yield was 61% in the case where $n^1=0$, $m^1=3$, M=Na, and $X^1=CO_2C_2H_5$; the yield was 63 to 65% in the case where $n^1=0$, $m^1=3$, M=K, and $X^1=CO_2C_2H_5$; and the yield was 51% in the case where $n^1=1$, $m^1=3$, M=K, and $X^1=CO_2C_2H_5$.

That is, both of these conventional processes give a yield at the level of 50%–60% only and hence neither of them is satisfactory as an industrial production process. Particularly in the former process, i.e., the flow process, the conversion rate cannot be increased because increasing the conversion rate lowers the selectivity. Therefore, this process is also disadvantageous in that it requires not only the separation of the desired product from unreacted starting materials but also recycling of the unreacted starting materials, making the operations troublesome.

JP-A-7-505164 discloses a process for obtaining a fluorinated vinyl ether of the general formula (II) by converting a carboxylic acid fluoride of the general formula (III) wherein $n^1=1$, $m^1=2$, and $X^1=CO_2CH_3$, to silyl ester and then reacting the silyl ester with KF at a high temperature. This process, however, cannot be regarded as an industrially excellent process because it requires a troublesome procedure and gives a yield of only 69%.

There has been no report suggesting a difference in the yield of a fluorinated vinyl ether of the general formula (II) wherein $X^1=CO_2R^1$ between the case where M is sodium in the general formula (IV) and the case where M is potassium in the general formula (IV). In fact, also in the Examples described in JP-A-52-78827 ($n^1=0$, $m^1=3$, and $X^1=CO_2C_2H_5$), there is no significant difference between the yield attained when M is sodium and the yield attained when M is potassium.

As described above, a process is known for producing a fluorinated vinyl ether represented by general formula (II) wherein $X^1=CO_2R^1$, in high yield by using a carboxylic acid fluoride of general formula (III) wherein $X^1=CO_2R^1$, as a starting material. The reaction results obtained according to the processes disclosed in the above known references are summarized below.

<Flow Process> (JP-A-53-132519)
  $n^1=1$, $m^1=2$, M=Na yield 67%,
  $n^1=2$, $m^1=2$, M=Na yield 61%.

<Two-Stage Process> (JP-A-52-78827)
  $n^1=0$, $m^1=3$, M=Na yield 61%,
  $n^1=0$, $m^1=3$, M=K yield 63 to 65%,
  $n^1=1$, $m^1=3$, M=K yield 51%.

Therefore, there has been a need for an economically more advantageous process for producing a fluorinated vinyl ether of the general formula (II) wherein $X^1=CO_2R^1$, in high yield from a carboxylic acid fluoride of general formula (III) wherein $X^1=CO_2R^1$, by a simple procedure.

As a process for producing a fluorinated vinyl ether of general formula (II) wherein $X^1=CO_2R^1$, besides the above-mentioned flow process and two-stage process, there have been proposed, for example, a process of treating a vinyl ether having a $CH_3OCF_2CF_2-$ group at the terminal with a strong acid to introduce an ester group (JP-A-60-156632), a process of esterifying a vinyl ether having a carboxylic acid fluoride at the terminal (JP-A-54-112822), and a process of dehalogenating a precursor having a $ICF_2CF_2O-$ structure to introduce a vinyl group (JP-A-55-31004). All of these processes, however, are not practical because they require troublesome operations and give a low yield.

Next, conventional techniques for producing a fluorinated vinyl ether monomer represented by the general formula (II) wherein $X^1=-SO_2F$ are described.

A typical process for producing said monomer includes a process in which a carboxylic acid fluoride of the general formula (III) wherein $X^1=-SO_2F$ is pyrolyzed in an alkali to produce the monomer. For example, JP-A-47-365 ($n^1=1$ and $m^1=2$) and JP-A-56-90054 ($n^1=0$, 1 and $m^1=3$) disclose processes which comprise feeding a carboxylic acid fluoride of the general formula (III) wherein $X^1=-SO_2F$ into sodium carbonate powder heated at 235 to 240° C., to pyrolyze the carboxylic acid fluoride, and then collecting the resulting vinyl ether monomer by cooling (the flow processes). In addition, a process is also known which comprises reacting a carboxylic acid fluoride of the general formula (III) wherein $X^1=-SO_2F$ ($n^1=1$ or 2 and $m^1=2$) with sodium carbonate to convert the carboxylic acid fluoride into the sodium salt of the carboxylic acid, and then heating the sodium salt to pyrolyze the same, to obtain a vinyl ether monomer (the two-stage process) (JP-B-41-7949).

In the flow processes disclosed in JP-A-47-365 and JP-A-56-90054, the conversion rate cannot be increased because increasing the conversion rate lowers the selectivity. Therefore, these processes cannot give a high yield. Furthermore, they are also disadvantageous in that they require not only separation of the desired product from unreacted starting materials but also recycling of the unreacted starting materials, making the operation troublesome. In addition, they are also disadvantageous in that in the pyrolysis using sodium carbonate, the $SO_2F$ group reacts with sodium carbonate at a high temperature, so that the yield is decreased. On the other hand, in the two-stage process in which the conversion to sodium salt is carried out and then its pyrolysis is conducted as in the process disclosed in JP-B-41-7949, remarkable side reactions take place, so that it is difficult to increase the yield.

The reaction results in the above known references are summarized below.

<Flow Processes> (JP-A-47-365 and JP-A-56-90054)
  $n^1=0$, $m^1=3$, M=Na yield 49%,
  $n^1=1$, $m^1=2$, M=Na yield 67%,
  $n^1=1$, $m^1=3$, M=Na yield 60%.

<Two-Stage Process> (JP-B-41-7949)
  $n^1=1$, $m^1=2$, M=Na yield 29%,
  $n^1=2$, $m^1=2$, M=Na yield 27%.

As described above, there has been no industrially useful process for producing a fluorinated vinyl ether of the general formula (II) wherein $X^1=-SO_2F$ from a carboxylic acid fluoride of the general formula (III) wherein $X^1=-SO_2F$, and there has been a need for a more economically advantageous production process which gives a high yield and requires only a simple procedure.

In addition, in the known references concerning the above conventional techniques, there is no discussion as to the difference between the yields attained by the use of a sodium salt and that attained by the use of a potassium salt as the compound of the general formula (IV) in the various processes for producing a fluorinated vinyl ether of the general formula (II) wherein $X^1=-SO_2F$ from a carboxylic acid fluoride of the general formula (III) wherein $X^1=-SO_2F$ via a carboxylate of the general formula (IV) wherein $X^1=-SO_2F$. Moreover, no specific example of the potassium salt has been reported therein.

The present invention solves the above problems and is intended to provide an economically advantageous process for producing a specific fluorinated vinyl ether among fluorinated vinyl ethers of the general formula (II) in high yield by a simple procedure.

DISCLOSURE OF THE INVENTION

The present inventors carried out studies in order to develop an economically advantageous process for producing a fluorinated vinyl ether of the general formula (II) in high yield by a simple procedure, and consequently found that a high-purity fluorinated vinyl ether with a specific structure among fluorinated vinyl ethers of the general formula (II) can be obtained at a high conversion rate and in high yield by treating a carboxylate with a specific structure among carboxylates of the general formula (II) under specific conditions, whereby the present invention has been accomplished. That is, the aspects of the present invention are as follows.

1. A process for producing a fluorinated vinyl ether represented by general formula (2), comprising:

pyrolyzing a carboxylic acid potassium salt represented by general formula (1) in the absence of a solvent:

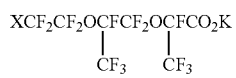

$$XCF_2CF_2OCFCF_2OCFCO_2K \quad (1)$$
$$\phantom{XCF_2CF_2O}|\phantom{CFCF_2O}|$$
$$\phantom{XCF_2CF_2O}CF_3\phantom{CF_2O}CF_3$$

wherein X is —$CO_2R$ or —$SO_2F$, and R is an alkyl group;

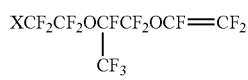

$$XCF_2CF_2OCFCF_2OCF=CF_2 \quad (2)$$
$$\phantom{XCF_2CF_2O}|$$
$$\phantom{XCF_2CF_2O}CF_3$$

wherein X is as defined in the general formula (1).

2. A process for producing a fluorinated vinyl ether represented by general formula (2) comprising:

pyrolyzing a carboxylic acid potassium salt represented by general formula (1) while maintaining the salt in the solid state.

3. A process for producing a fluorinated vinyl ether represented by general formula (2), comprising:

pyrolyzing a carboxylic acid potassium salt represented by general formula (1) in the absence of a solvent while maintaining the salt in the solid state.

4. The production process according to any one of items 1 to 3, wherein the fluorinated vinyl ether of general formula (2) produced is collected outside the reaction system.

5. The production process according to any one of items 1 to 4, wherein the pyrolysis of the carboxylic acid potassium salt represented by general formula (1) is carried out under reduced pressure.

6. The production process according to any one of items 1 to 5, wherein the carboxylic acid potassium salt represented by the general formula (1) is derived from a carboxylic acid fluoride represented by general formula (3):

$$XCF_2CF_2OCFCF_2OCFCOF \quad (3)$$
$$\phantom{XCF_2CF_2O}|\phantom{CFCF_2O}|$$
$$\phantom{XCF_2CF_2O}CF_3\phantom{CF_2O}CF_3$$

wherein X is as defined in general formula (1).

7. The production process according to item 6, wherein as the carboxylic acid fluoride represented by the general formula (3), one having a purity of 80% by weight or more is used.

8. The production process according to item 6, wherein as the carboxylic acid fluoride represented by the general formula (3), one having a purity of 90% by weight or more is used.

9. The production process according to item 7, wherein the carboxylic acid fluoride represented by the general formula (3) contains one or more impurities represented by general formula (4):

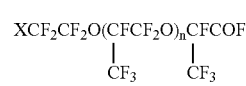

$$XCF_2CF_2O(CFCF_2O)_nCFCOF \quad (4)$$
$$\phantom{XCF_2CF_2O(}|\phantom{CFCF_2O)_n}|$$
$$\phantom{XCF_2CF_2O(}CF_3\phantom{CF_2O)_n}CF_3$$

wherein n is 0 or an integer of 2 or more, and X is as defined in general formula (1), and the total content of the impurities is less than 20% by weight.

10. The production process according to item 8, wherein when the carboxylic acid fluoride represented by general formula (3) contains one or more impurities represented by general formula (4), the total content of the impurities is less than 10% by weight.

11. The production process according to 1 to 10, wherein X is —$CO_2R$ in general formula (1) and general formula (2).

12. The production process according to any one of items 1 to 10, wherein X is —$SO_2F$ in the general formula (1) and the general formula (2).

BEST MODE FOR CARRYING OUT THE INVENTION

The production process of the present invention comprises a process for producing a fluorinated vinyl ether of general formula (II) wherein $n^1=1$ and $m^1=2$ (i.e., a fluorinated vinyl ether of the general formula (2)) from a carboxylate of the general formula (IV) wherein $n^1=1$, $m^1=2$ and M=a potassium atom (i.e., a carboxylate of the general formula (1)), wherein reaction conditions for the production are specified so that a high conversion rate can be achieved and moreover, the reaction yield is specifically increased. The specific reaction conditions are as follows: 1) in the first place, the process is the two-stage process, not the flow process, and 2) the pyrolysis of said carboxylate is carried out in the absence of a solvent and/or while maintaining the carboxylate in a solid state.

The present inventors closely investigated the various conventional processes, whose reaction results are described above, and consequently found the following: in many cases, carboxylates represented by general formula (IV) are in a molten or wet state at their pyrolysis temperature or a lower temperature, and the pyrolysis reaction of the carboxylate in such a state yields a remarkable amount of side reaction products, resulting in the decreased yield of the desired product. It was found that, for example, when $X^1=CO_2R^1$ in general formula (IV), a large amount of a diester compound (V):

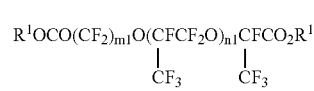

$$R^1OCO(CF_2)_{m1}O(CFCF_2O)_{n1}CFCO_2R^1 \quad (V)$$
$$\phantom{R^1OCO(CF_2)_{m1}O(}|\phantom{CFCF_2O)_{n1}}|$$
$$\phantom{R^1OCO(CF_2)_{m1}O(}CF_3\phantom{CF_2O)_{n1}}CF_3$$

wherein $n^1$, $m^1$ and $R^1$ are as defined in general formula (II), is produced as a side reaction product by esterification of a carboxylic acid fluoride of general formula (III) to lower the yield of a desired product.

It is presumed that the aforesaid diester compound (V) is produced by either transesterification between the molecules of the carboxylate of general formula (IV) in a molten or wet state, or transesterification between the carboxylate of general formula (IV) in a molten or wet state and the starting material of general formula (III) in the reaction.

Therefore, the present inventors have conducted studies to develop a process for producing a fluorinated vinyl ether of the general formula (II) in high yield by suppressing the side reactions described above.

At first, the present inventors closely investigated the characteristics of various kinds of carboxylates represented by general formula (IV), and consequently found that although most of the carboxylates assume a molten state at their pyrolysis reaction (decarboxylation) temperature or a lower temperature, carboxylates in which $\{n^1=1, m^1=2$ and $M=K\}$ (i.e., carboxylates of the general formula (1)) among the others assume a solid state even at their pyrolysis reaction (decarboxylation) temperature. In the present specification, the term "solid state" means a non-fluid state.

On the other hand, in all of the carboxylates of the general formula (IV) used in reaction examples for which the yields are described in the known references described above, a combination of $\{n^1, m^1$ and $M\}$ is other than $\{n^1=1, m^1=2$ and $M=K\}$. Many of these carboxylates of the general formula (IV) in the known references assume a molten or wet state at their pyrolysis reaction (decarboxylation) temperature or a lower temperature as described above. It is presumed that such a property of the carboxylates hinders the increase of the yield of a fluorinated vinyl ether of the general formula (II).

Next, the present inventors found that when a carboxylate of the above general formula (IV) wherein $\{n^1=1, m^1=2$ and $M=K\}$ (i.e., a carboxylate of the general formula (1)) is pyrolyzed in the absence of a solvent and/or while maintaining the carboxylate in the solid state, a corresponding fluorinated vinyl ether of the general formula (II) (i.e., a fluorinated vinyl ether of the general formula (2)) can be produced in high yield, whereby the present invention has been accomplished. Although the reason why such a high yield can be attained in the reaction method according to the present invention is not clear, the following is presumed as a possibility: the reason is that the side reaction between molecules, a problem in conventional methods, is suppressed in the pyrolysis reaction of said carboxylate in the solid state.

Although the potassium salt of the general formula (1) used in the present invention (i.e., the carboxylate of the general formula (IV) wherein $\{n^1=1, m^1=2$ and $M=K\}$) may be produced by any process, a potassium salt obtained by conversion from a carboxylic acid fluoride of above general formula (3) is preferred because of its high quality. As to a method for converting the carboxylic acid fluoride of general formula (3) to the potassium salt, it is sufficient that the carboxylic acid fluoride is reacted with an alkali containing a potassium atom in a solvent or without solvent. Specific examples of the alkali containing a potassium atom include potassium carbonate, potassium hydrogencarbonate, potassium hydroxide, potassium phosphate, potassium acetate, etc. Potassium carbonate is preferred because the counter ion component for potassium can be removed as a gas. The potassium carbonate may be particulate, powdery, or finely powdered, or particulate, powdered or finely powdered with an increased specific surface area by having pores, or the like. In addition, the potassium carbonate is preferably thoroughly dried before use. When a solvent is used in the above-mentioned reaction of the carboxylic acid fluoride with the alkali, a polar solvent is generally used. Specific examples of the polar solvent are water; alcohols, such as methanol, ethanol, propanol, etc.; ethers, such as tetrahydrofuran, dioxane, ethylene glycol dimethyl ether, diethylene glycol dimethyl ether, etc.; nitriles, such as acetonitrile, propionitrile, etc.; amides, such as dimethylformamide, dimethylacetamide, etc.; and dimethyl sulfoxide. These solvents must be removed after the reaction, and an easily removable solvent having a boiling point of 100° C. or lower is preferred. As the solvent, an aprotic polar solvent is more preferred because a protonated $CF_3CHF-$ group is formed in some cases instead of a trifluorovinyl group if a protic solvent remains at the time of the pyrolysis. Solvents satisfying these conditions include tetrahydrofuran, ethylene glycol dimethyl ether, acetonitrile and the like. In addition, when a solvent is used in the above-mentioned reaction of the carboxylic acid fluoride with the alkali, the reaction temperature is preferably within a range of 0 to 80° C., more preferably within a range of 20 to 60° C., for the suppression of side reactions. It is also possible to carry out the above-mentioned reaction of the carboxylic acid fluoride with the alkali in the absence of a solvent. In this case, it is especially preferred to carry out the reaction with potassium carbonate in the absence of a solvent so that the counter ion component for potassium does not remain after the reaction. In this case, the reaction temperature is preferably 50 to 150° C., more preferably 80 to 120° C.

When X is $-CO_2R$ in the general formula (3), although the above-mentioned reaction with the alkali can be carried out either in the presence or in the absence of a solvent, the reaction is preferably carried out in the absence of a solvent in order to simplify the reaction operation. On the other hand, also when X is $-SO_2F$ in the general formula (3), the above-mentioned reaction with the alkali can be carried out either in the presence or absence of a solvent, but a solvent is preferably used in order to prevent a side reaction at the $-SO_2F$ group.

As to the amount of the alkali used for the conversion to the potassium salt, the alkali is used in an amount of equivalent(s) necessary for the complete conversion of the acid fluoride to the potassium salt. However, when X is $-CO_2R$, an excessive amount of the alkali can be used, if necessary. For example, potassium carbonate can be used in an amount in a range of generally 1 to 4 equivalents, preferably 1 to 2 equivalents.

In the production process of the present invention, the acid fluoride of general formula (3) used preferably has a high purity. If the acid fluoride (3) contains impurities, side reactions tend to take place, resulting in a decreased yield. For substantial removal of such an influence of the impurities, the purity of the acid fluoride (3) is preferably 80% by weight or more, more preferably 90% by weight or more, still more preferably 95% by weight or more. Although how the impurities in the acid fluoride (3) affect the decrease of the yield is not definitely known, it is assumed to be due to, for example, the depression of melting point of the potassium salt of general formula (1) caused by contamination with an impurity component or a salt thereof; the partial wetting or liquefaction of the potassium salt of general formula (1) caused by mutual solubilization between an impurity component or a salt thereof and the potassium salt; and a secondary side reaction of the potassium salt of the general formula (1) or a decomposition product thereof with an impurity component or a decomposition product thereof.

In addition, when the acid fluoride of general formula (3) is produced, acid fluorides of the general formula (4):

wherein n is 0 or an integer of 2 or more and X is as defined in general formula (1), are generally produced as by-products. Therefore, contamination with these acid fluorides as impurities may occur. That is, when the acid fluoride (3) contains the compounds of general formula (4) as impurities, the amount of these compounds is preferably less than 20% by weight, more preferably less than 10% by weight, still more preferably less than 5% by weight.

For the same reason as in the case of the above-mentioned purity of the acid fluoride (3), the purity of the carboxylic acid potassium salt of the general formula (1) used in the production process of the present invention is preferably 80% by weight or more, more preferably 90% by weight or more, still more preferably 95% by weight or more.

In the production process of the present invention, when X=—CO$_2$R in the above general formula (3), an alkyl group R preferably has a small number of carbon atoms for easy purification by distillation. A lower alkyl group having 1 to 4 carbon atoms is usually employed. Specific examples of R include a methyl group, ethyl group, propyl group, isopropyl group, n-butyl group, etc. Of these, a methyl group and ethyl group are preferred, and a methyl group is especially preferred.

The potassium salt of the general formula (1) is decarboxylated by heating at a temperature higher than its pyrolysis temperature to give the vinyl ether (2). Although this pyrolysis itself proceeds either in a solvent or in the absence of a solvent, in order to suppress side reactions to increase the yield, the pyrolysis must be carried out without a solvent and/or while maintaining the potassium salt of general formula (1) in a solid state. In this case, a nonpolar solvent, such as a hydrocarbon solvent or a fluorinated hydrocarbon solvent, or a solvent having no ability to dissolve the carboxylic acid potassium salt used in the present invention, though having a polar group, such as a fluorinated ether solvent may be present in the reaction system used in the present invention, so long as it does not hinder the retention of the solid state of the potassium salt of general formula (1). On the other hand, a polar solvent is not preferred because if it is present in a large amount, it causes remarkable side reactions and hence a decrease of the yield of the fluorinated vinyl ether probably because it dissolves the carboxylic acid potassium salt used in the present invention. Even a polar solvent, however, may be present in such a small amount that the carboxylic acid potassium salt can retain a substantially solid state at its pyrolysis temperature. That is, the term "in the absence of a solvent" used herein means that a solvent component is not contained in such an amount that it substantially changes the properties of the potassium salt of general formula (1). For example, a solvent component such as a solvent used for producing the potassium salt of the above general formula (1) may be contained in an amount of 5% by weight or less, preferably 3% by weight or less, based on the weight of said potassium salt. Although the heating temperature may be any temperature at which the decarboxylation proceeds, the heating is conducted at generally 120 to 300° C., preferably 150 to 250° C. During the pyrolysis, it is preferred to prevent the vinyl ether produced as a liquid or gas from being retained in the system. The vinyl ether is preferably rapidly guided out of the reaction system to be collected with a condenser or the like. The vinyl ether is more preferably removed from the system by a method such as reducing the pressure in the system, allowing an inert gas to flow, or the like. Especially preferred is a method in which the vinyl ether is forcedly drawn out of the system under reduced pressure. When the pyrolysis is carried out under reduced pressure, the pressure in the system is preferably $4.0 \times 10^4$ Pa or less, more preferably $2.7 \times 10^4$ Pa or less, in particular, $1.3 \times 10^4$ Pa or less.

The fluorinated vinyl ether produced by the process of the present invention is obtained in high yield and, moreover, with high purity because it hardly contains unreacted acid fluoride owing to a high conversion rate and no remarkable side reaction takes place. Therefore, the fluorinated vinyl ether obtained by the production process of the present invention is characterized in that its purification after the reaction is very easy.

As described above, the production process of the present invention is industrially very useful because it makes it possible to produce the fluorinated vinyl ether used as a starting material for an ion-exchange membrane for sodium chloride electrolysis or a diaphragm for a fuel cell, in high yield by simple operations. Furthermore, the fluorinated vinyl ether produced by the process of the present invention is characterized in that its purity is high and that its purification as a subsequent step is easy.

The present invention will be described by way of the following examples. The reaction yields were calculated by conversion for the purity of a starting material. The yield was calculated as the proportion of the number of moles of the product with respect to the number of moles of the starting material.

EXAMPLE 1

Into a 100-ml flask were introduced 14.5 g of potassium carbonate and 20 ml of ethylene glycol dimethyl ether, and 48.8 g of a carboxylic acid fluoride (purity 96% by weight) of general formula (3) wherein X=—CO$_2$CH$_3$ was added dropwise thereto at 40° C. The resulting mixture was continuously stirred as it was for 2 hours, after which the solvent was distilled off under reduced pressure and the residue was dried in a vacuum at 100° C. to obtain a solid potassium salt containing KF. The complete conversion of the carboxylic acid fluoride to the corresponding potassium salt was confirmed by $^{19}$F-NMR. The flask was equipped with a distillation head and a condenser and heated as it was up to 200° C. at atmospheric pressure, and the heating was continued at 200° C. until distilling-out of a liquid ceased. During the heating, the potassium salt retained its solid state. By gas chromatography, 38.3 g of the liquid recovered was analyzed to find that it contained a vinyl ether of general formula (2) wherein X=—CO$_2$CH$_3$ in an amount corresponding to a purity of 96% by weight (yield: 91%). In addition, the liquid contained 2% by weight of a diester of formula (V).

EXAMPLE 2 (COMPARATIVE EXAMPLE)

A reaction was carried out in the same manner as in Example 1, except that 11.1 g of sodium carbonate was used in place of potassium carbonate. A sodium salt obtained by distilling off the solvent was a viscous liquid. By gas chromatography, 35.3 g of a liquid obtained by the pyrolysis was analyzed to find that the purity of the vinyl ether was 80% by weight (yield: 66%), and that this liquid contained 17% by weight of a diester of formula (V):

EXAMPLE 3 (COMPARATIVE EXAMPLE)

In this example, the vinyl ether was synthesized by the flow process.

Into a 200-ml three-necked flask was introduced 18.5 g of potassium carbonate, and heated at 220° C. Thereinto was dropped 48.8 g of the same carboxylic acid fluoride as used in Example 1, in small portions. The gaseous product was collected with a condenser, and 39.2 g of the resulting liquid was analyzed by gas chromatography to find that the liquid contained 65% by weight of the vinyl ether (yield: 61%, and selectivity: 76%), 25% by weight of unreacted carboxylic acid fluoride and 1% by weight of a diester of formula (V).

EXAMPLE 4 (COMPARATIVE EXAMPLE)

A reaction was carried out in the same manner as in Example 3, except that 14.2 g of sodium carbonate was used in place of potassium carbonate. By gas chromatography, 40.3 g of the resulting liquid was analyzed to find that the liquid contained 68% by weight of the vinyl ether (yield: 64%, and selectivity: 72%), 13% by weight of unreacted carboxylic acid fluoride and 9% by weight of a diester of the formula (V).

EXAMPLE 5

Into a 200-ml three-necked flask was introduced 27.6 g of potassium carbonate, and 48.8 g of the same carboxylic acid fluoride (purity 95% by weight) as in Example 1 was added dropwise thereto at 100° C. The reaction was continued for another 2 hours, whereupon the whole reaction mixture was solidified. At this stage, the complete conversion of the carboxylic acid fluoride to the corresponding potassium salt was confirmed by $^{19}$F-NMR. The flask was equipped with a distillation head and a condenser and heated as it was up to 200° C. to carry out a pyrolysis reaction. By gas chromatography, 39.5 g of the resulting liquid was analyzed to find that the liquid contained 91% by weight of the vinyl ether (yield: 89%) and 4% by weight of a diester of formula (V).

EXAMPLE 6 (COMPARATIVE EXAMPLE)

A reaction was carried out in the same manner as in Example 1, except that 32.2 g of CH$_3$OCOCF$_2$CF$_2$OCF(CF$_3$)COF (purity: 93% by weight) was used in place of the carboxylic acid fluoride of general formula (3) wherein X=—CO$_2$CH$_3$. In the course of this procedure, the complete conversion of CH$_3$OCOCF$_2$CF$_2$OCF(CF$_3$)COF to the corresponding potassium salt was confirmed by $^{19}$F-NMR. On heating to 200° C., the potassium salt decomposed while vigorously generating white smoke. The heating was continued at 200° C. until distilling-out of a liquid ceased. By gas chromatography, 15.7 g of the liquid recovered was analyzed to find that it was a complicated mixture containing a small amount of a vinyl ether of general formula (II) wherein n$^1$=0, m$^1$=2 and X$^1$=—CO$_2$CH$_3$.

EXAMPLE 7 (COMPARATIVE EXAMPLE)

A reaction was carried out in the same manner as in Example 6, except that 11.1 g of sodium carbonate was used in place of potassium carbonate. A sodium salt produced in the course of this procedure was a viscous liquid. By gas chromatography, 16.5 g of the liquid obtained by the pyrolysis was analyzed to find that it was a complicated mixture containing a small amount of the same vinyl ether as in Example 6.

EXAMPLE 8 (COMPARATIVE EXAMPLE)

A reaction was carried out in the same manner as in Example 1, except that 53.8 g of a carboxylic acid fluoride (purity: 95% by weight) of general formula (III) wherein n$^1$=1, m$^1$=3 and X$^1$=—CO$_2$CH$_3$ was used in place of the carboxylic acid fluoride used in Example 1 and that 11.1 g of sodium carbonate was used in place of potassium carbonate. A sodium salt obtained by distilling off the solvent was a viscous liquid. By gas chromatography, 39.2 g of the liquid obtained by the pyrolysis was analyzed to find that the purity of a vinyl ether of general formula (II) wherein n$^1$=1, m$^1$=3 and X$^1$=—CO$_2$CH$_3$ was 73% by weight (yield: 64%), and that this liquid contained 18% by weight of a diester compound.

EXAMPLE 9

Into a 200-ml three-necked flask were introduced 51.2 g of a carboxylic acid fluoride (purity: 98% by weight) of the general formula (3) wherein X=—SO$_2$F and 20 ml of ethylene glycol dimethyl ether, and 14.5 g of potassium carbonate was added thereto in small portions with heating at 60° C. In addition, the reaction mixture was continuously stirred at 60° C. for 30 minutes and then the solvent was distilled off under reduced pressure to obtain a solid potassium salt containing KF. The conversion rate calculated on the basis of $^{19}$F-NMR was 96%. The flask was equipped with a distillation head and a condenser and heated as it was up to 220° C. at atmospheric pressure, and the heating was continued at 220° C. until distilling-out of a liquid ceased. During the heating, the potassium salt retained its solid state. By gas chromatography, 42.9 g of the liquid recovered was analyzed to find that it contained 84% by weight of a vinyl ether of the general formula (2) wherein X=—SO$_2$F (crude yield calculated without conversion for the purity of the starting material: 81%, and yield: 83%).

EXAMPLE 10

Into a 200-ml three-necked flask were introduced 13.8 g of potassium carbonate and 20 ml of ethylene glycol dimethyl ether, and 51.2 g of the same carboxylic acid fluoride as in Example 9 was added dropwise thereto under stirring at 40° C. After the reaction was continued for another 1 hour, the solvent was distilled off under reduced pressure to obtain a solid potassium salt containing KF. The conversion rate calculated on the basis of $^{19}$F-NMR was 93%. Pyrolysis was carried out at 220° C. in the same manner as in Example 9, and 40.3 g of the liquid recovered was analyzed by gas chromatography to find that it contained 91% by weight of the vinyl ether (crude yield calculated without conversion for the purity of the starting material: 82%, and yield: 84%).

EXAMPLE 11

A reaction was carried out by the same method as in Example 10, except that acetonitrile was used in place of ethylene glycol dimethyl ether. The conversion rate of the potassium salt calculated on the basis of $^{19}$F-NMR was 96%. Pyrolysis was carried out at 220° C. in the same manner as in Example 9, and 40.3 g of the liquid recovered was analyzed by gas chromatography to find that it contained 92% by weight of the vinyl ether (crude yield calculated without conversion for the purity of the starting material: 83%, and yield: 85%).

EXAMPLE 12 (COMPARATIVE EXAMPLE)

A reaction was carried out in the same manner as in Example 10, except that 10.6 g of sodium carbonate was used in place of potassium carbonate. A sodium salt obtained by distilling off the solvent was a viscous liquid, and the conversion rate calculated on the basis of $^{19}$F-NMR was 99%. The pyrolysis proceeded at 200° C. and 41.2 g of the resulting liquid was analyzed by gas chromatography to find that it contained 70% by weight of the vinyl ether (crude yield calculated without conversion for the purity of the starting material: 65%, and yield: 66%).

EXAMPLE 13 (COMPARATIVE EXAMPLE)

Into a 200-ml three-necked flask was introduced 10.6 g of sodium carbonate, and heated at 220° C. Thereinto was dropped 51.2 g of the same carboxylic acid fluoride as in Example 9 in small portions. The product was collected with a condenser, and 48.4 g of the resulting liquid was analyzed by gas chromatography to find that the liquid contained 20% by weight of the vinyl ether (crude yield calculated without conversion for the purity of the starting material: 22%, yield: 22%, and selectivity: 70%), and 72% by weight of unreacted acid fluoride.

EXAMPLE 14

After the carboxylic acid potassium salt was prepared in the same manner as in Example 5, the flask was equipped with a distillation head and a condenser and heated to 160° C. at a pressure of $1.3 \times 10^4$ Pa to initiate a pyrolysis reaction. The reaction was carried out until distilling-out of a liquid ceased, while reducing the pressure in the reactor gradually to $2.6 \times 10^3$ Pa over a period of 6 hours. During the reaction, the potassium salt retained its solid state. By gas chromatography, 41.4 g of the liquid recovered was analyzed to find that it contained a vinyl ether of the general formula (2) wherein X=—$CO_2CH_3$ in an amount corresponding to a purity of 97% by weight (yield: 95%). In addition, the liquid contained 1% by weight of a diester of the formula (V).

EXAMPLE 15

A reaction was carried out in the same manner as in Example 5, except that the carboxylic acid fluoride with a purity of 74% (containing 18% by weight of a compound of general formula (4) wherein n=2 and X=—$CO_2CH_3$) was used. The potassium salt was a rice-cake-like solid at 100° C. When this solid was slowly heated, it came to be gruel-like at 180° C. The gruel-like material was pyrolyzed at 200° C., and 30.2 g of the resulting liquid was analyzed by gas chromatography to find that it contained 74% by weight of a vinyl ether of general formula (2) (yield: 72%) and 12% by weight of a diester of formula (V).

INDUSTRIAL APPLICABILITY

The production process of the present invention is industrially very useful because it makes it possible to produce a fluorinated vinyl ether used as a starting material for an ion-exchange membrane for sodium chloride electrolysis or a diaphragm for a fuel cell, in high yield by simple operations. Furthermore, the vinyl ether produced by the process of the present invention is characterized in that its purity is high and that its purification as a subsequent step is easy.

What is claimed is:

1. A process for producing a fluorinated vinyl ether represented by formula (2), comprising:
    pyrolyzing a carboxylic acid potassium salt represented by formula (1) in the absence of a solvent wherein formula (1) and formula (2) are as follows:

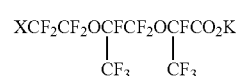

wherein X is —$CO_2R$ or —$SO_2F$, and R is an alkyl group; and

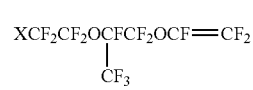

wherein X is as defined in the formula (1).

2. A process for producing a fluorinated vinyl ether represented by formula (2) comprising:
    pyrolyzing a carboxylic acid potassium salt represented by formula (1) while maintaining the salt in the solid state, wherein formula (1) and formula (2) are as follows:

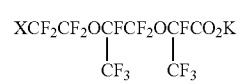

wherein X is —$CO_2R$ or —$SO_2F$, and R is an alkyl group; and

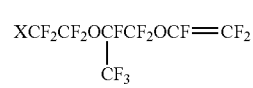

wherein X is as defined in the formula (1).

3. A process for producing a fluorinated vinyl ether represented by formula (2) comprising:
    pyrolyzing a carboxylic acid potassium salt represented by formula (1) in the absence of a solvent while maintaining the salt in the solid state, wherein formula (1) and formula (2) are as follows:

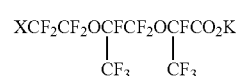

wherein X is —$CO_2R$ or —$SO_2F$, and R is an alkyl group; and

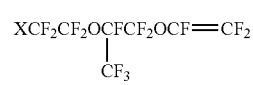

wherein X is as defined in the formula (1).

4. The production process according to any one of claims 1 to 3, wherein the fluorinated vinyl ether of formula (2) produced is recovered from the reaction system.

5. The production process according to any one of claims 1 to 3, wherein the pyrolysis of the carboxylic acid potassium salt represented by formula (1) is carried out under reduced pressure.

6. The production process according to any one of claims 1 to 3, wherein the carboxylic acid potassium salt represented by formula (1) is derived from a carboxylic acid fluoride represented by formula (3), wherein formula (3) is:

(3)

wherein X is as defined in formula (1).

7. The production process according to claim 6, wherein X is —$CO_2R$ in formula (1) and formula (3), and the carboxylic acid potassium salt represented by formula (1) is derived from the carboxylic acid fluoride represented by formula (3) in the absence of a solvent.

8. The production process according to claim 6, wherein as the carboxylic acid fluoride represented by formula (3), one having a purity of 80% by weight or more is used.

9. The production process according to claim 6, wherein as the carboxylic acid fluoride represented by formula (3), one having a purity of 90% by weight or more is used.

10. The production process according to claim 8, wherein the carboxylic acid fluoride represented by formula (3) contains one or more impurities represented by formula (4), wherein formula (4) is as follows:

(4)

wherein n is 0 or an integer of 2 or more, and X is as defined in formula (1), and the total amount of the impurities is more than 0% and less than 20% by weight.

11. The production process according to claim 9, wherein when the carboxylic acid fluoride represented by formula (3) contains one or more impurities represented by formula (4), the total amount of the impurities is more than 0% and less than 10% by weight.

12. The production process according to any one of claims 1 to 3, wherein X is —$CO_2R$ in formula (1) and formula (2).

13. The production process according to any one of claims 1 to 3, wherein X is —$SO_2F$ in formula (1) and formula (2).

* * * * *